(12) United States Patent
Du

(10) Patent No.: US 7,418,074 B2
(45) Date of Patent: Aug. 26, 2008

(54) COMPUTED TOMOGRAPHY SYSTEM WITH ADJUSTABLE FOCAL SPOT-TO-DETECTOR DISTANCE

(75) Inventor: Jian Du, Shanghai (CN)

(73) Assignee: Siemens Aktiengesellschaft, Munich (DE)

( * ) Notice: Subject to any disclaimer, the term of this patent is extended or adjusted under 35 U.S.C. 154(b) by 142 days.

(21) Appl. No.: 11/392,087

(22) Filed: Mar. 29, 2006

(65) Prior Publication Data

US 2006/0222143 A1    Oct. 5, 2006

(30) Foreign Application Priority Data

Mar. 31, 2005    (CN) .................... 2005 2 0011180 U

(51) Int. Cl.
*A61B 6/03* (2006.01)

(52) U.S. Cl. ........................................................ 378/13

(58) Field of Classification Search .................... 378/11, 378/13, 197

See application file for complete search history.

(56) References Cited

U.S. PATENT DOCUMENTS

| 4,115,696 A * | 9/1978 | Truscott ..................... 378/197 |
| 5,095,501 A * | 3/1992 | Kobayashi ................. 378/196 |
| 6,814,489 B2 * | 11/2004 | Jensen et al. ............... 378/197 |

* cited by examiner

*Primary Examiner*—Chih-Cheng G Kao
(74) *Attorney, Agent, or Firm*—Schiff Hardin LLP

(57) ABSTRACT

A computed tomography system with an adjustable focal spot-to-detector distance has a gantry provided with a patient opening, an x-ray tube and a detector, respectively mounted at opposite sides of the gantry. The x-ray tube has a focal spot and the x-ray fan beam radiated from the focal spot exhibits a fixed aperture angle. The x-ray tube is installed on a linear track and can be moved along the rail of the linear track.

10 Claims, 1 Drawing Sheet

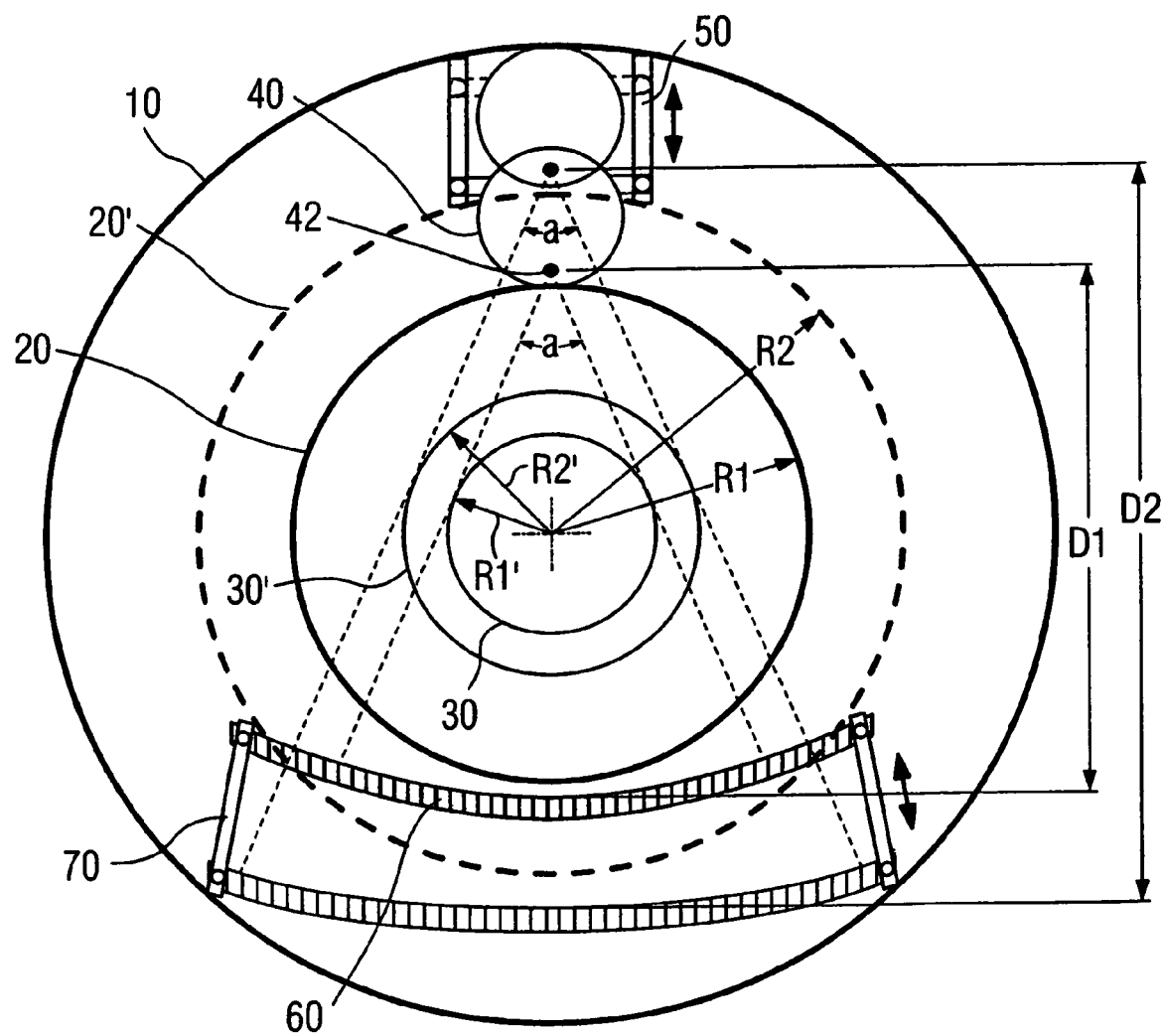

COMPUTED TOMOGRAPHY SYSTEM WITH ADJUSTABLE FOCAL SPOT-TO-DETECTOR DISTANCE

BACKGROUND OF THE INVENTION

1. Field of the Invention

The present invention concerns a computed tomography (CT) system, in particular a computed tomography system with an adjustable focal spot-to-detector distance.

2. Description of the Prior Art

In a conventional CT system, the aperture angle of the x-ray fan beam radiated by the x-ray tube and the distance between the focal spot of the x-ray tube and its corresponding detector are fixed. Not only does the accessibility to the patient during the scan process thereby decrease, but this can also lead to an impairment of the imaging quality of the system due to differences between volumes of patients (body parts) to be scanned, or differences in the quantities of the emitted/received x-rays.

In a typical CT system, a patient opening is mounted at a gantry in which a patient can be moved for scanning in the gantry. The x-ray tube is mounted on one side of the gantry and the focal spot of the x-ray tube exhibits a fixed aperture angle a of the emitted x-ray fan. A detector associated with the x-ray tube is provided on the detector mounting fastened on the other side of the gantry in order to receive x-ray radiation emitted by the focal spot for a system imaging.

Since the aperture angle of the x-ray fan emitted by the focal spot of the x-ray tube and the distance between the focal spot and the detector are fixed, the scanning of the patient within the patient opening is very uncomfortable when the volume of a patient to be scanned is extremely large, and the x-rays possibly do not entirely cover the volume of the patient in the FOV—field of view. If an x-ray tube with a larger aperture angle of the fan beam is used in order to overcome the such problems above, the cost of the apparatus rises significantly. If the diameter of the patient opening is increased in order to obtain a better accessibility to a patient to be scanned but the volume of the patient to be scanned is comparably small (for example a child), the amount of the x-rays passing through the patient and acquired by the detector significantly decreases, which seriously influences the quality of the imaging, although the impairment of the image quality can be partially compensated by subsequent image enhancement algorithms.

Designing a computed tomography system with an adjustable focal spot-to-detector distance is therefore a problem needing a solution in this field.

SUMMARY OF THE INVENTION

An object of the present invention is to provide a computed tomography system with an adjustable focal spot-to-detector distance.

This object is achieved in accordance with the present invention by a computed tomography system having a gantry provided with a patient opening, an x-ray tube and a detector, the x-ray tube and the detector being respectively attached at opposite sides of the gantry. The x-ray tube has a focal spot and the x-ray fan beam radiated from the focal spot exhibits a fixed aperture angle. The x-ray tube is installed on a linear track guide and is moveable along the rail of the linear track. The detector can be arranged on a detector mount for reception of x-rays, and the detector mount can be installed on a further linear track so as to be moveable along the rail of the further linear track. By controlling the rail length of both linear tracks, the displacement length of each of the x-ray tube and of the detector mount in the respective linear tracks can be determined. For example, telescopic rails can be provided for this purpose.

In a further embodiment an inner enclosure cladding defining the patient opening on the gantry side can be displaced such that the radius of the patient opening can be varied. The displacement of the inner enclosure can be coupled to the movement of the x-ray tube and/or the detector mount such that, given movement of the x-ray tube and/or of the detector mount, the maximal possible radius of the patient opening can be adjusted. The inner enclosure preferably is controlled simultaneously with the movement of the x-ray tube and/or of the detector mount, such that the adaptation ensues in a single step. Here it is particularly advantageous when both the x-ray tube and the detector mount are directed in linear tracks and both the x-ray tube and the detector mount and the inner enclosure are movement-coupled such that a uniform adaptation of the computed tomography system can occur. The inner enclosure can be formed by movement-coupled, overlapping lamella elements. In an embodiment, the patient opening can be enlarged in its radius, in a manner comparable to the aperture of an iris diaphragm of a camera.

The present invention can be applied in a number of types of computed tomography systems, in particular in spiral computed tomography systems.

With the present invention, the distance between the focal spot of the x-ray tube and its detector can be freely set by respectively installing of the x-ray tube and the detector mount of the CT system on the linear track on both sides of the gantry, which is how the advantages listed below can be achieved:

1. the acquisition field of the CT system can be enlarged with increasing distance between the x-ray tube and the detector mount;
2. by adjustment of the distance between the x-ray tube and the detector mount, more x-rays can effectively penetrate through a subject to be scanned, such that a higher system imaging quality can be attained, and
3. with increased diameter of the patient opening, a subject to be scanned with a larger volume can be inserted into the gantry for scanning or a better accessibility to a subject to be scanned can be achieved.

An adjustment of the distance between the focal spot and the detector on the basis of the dimension of a subject to be scanned is thus realized in real time by the present invention; the dependency of the image quality on the dimension of a subject to be scanned is reduced, whereby the clinical application range of the CT system is significantly expanded and a patient opening that can be expanded similar to the diaphragm of a camera is simultaneously provided by the invention.

DESCRIPTION OF THE DRAWINGS

The FIGURE is a schematic drawing of a section through the gantry of a computed tomography system with an adjustable focal spot-to-detector distance according to the present invention.

DESCRIPTION OF THE PREFERRED EMBODIMENTS

As shown in the FIGURE, the gantry 10 of the CT system has a patient opening 20, allowing a patient to be scanned to be introduced into the gantry 10 through the patient opening 20 with a radius of R1. An x-ray tube 40 is installed on one side of the gantry 10 and has a focal spot 42. The x-ray fan beam emitted by the focal spot 42 has a fixed aperture angle a. A detector mount 60 is installed on the other side of the gantry 10 opposite the x-ray tube 40. A detector for reception of x-rays emitted by the focal spot 42 is disposed on the detector mount 60. The distance between the focal spot 42 of the x-ray tube 40 and of the detector mount 60 is D1. Dependent on the fixed aperture angle a of the x-ray fan beam emitted by the focal spot 42 and the distance D1, the scan area 30 of the x-ray tube 40 in the patient opening 20 exhibits a radius of R1'.

So that the distance between the focal spot 42 of the x-ray tube 40 and the patient can be flexibly adjusted according to the volume of a patient to be scanned (under the condition that the aperture angle of the x-ray fan beam emitted by the focal spot 42 is fixed) so that as many x-rays as possible pass through the patient and can be acquired by the detector at the detector mount 60 (so an optimally high system imaging quality is attained), the computed tomography system with an adjustable focal spot-to-detector distance according to the invention provides a linear track 50 within the gantry 10. The x-ray tube 40 is installed on the linear track 50 and can move up and down along the rail of the linear track 50, such that the distance between the focal spot 42 of the x-ray tube 40 and the detector mount 60 can be adjusted.

When (as the FIGURE shows) the x-ray tube 40 moves along the linear track 50 to the position shown dashed, the distance between its focal spot 42 and the detector mount 60 changes to D1 plus the displacement by which it moves along the linear track 50, and the scan area of the x-ray tube 40 in the patient opening 20 changes from 30 to 30', and the radius R1' increases to R2', and the region covered by the x-rays emitted from the focal spot 42 of the x-ray tube 40 as well as the acquisition field of the CT system increase in size.

The displacement length on the linear track 50 of the x-ray tube 40 can clearly be determined by controlling the length of the of the rail of the linear track 50, such that the distance between the focal spot 42 of the x-ray tube 40 and the detector mount 60 can be freely adjusted in order to adapt the scanning to patients with various volumes. As much x-ray radiation as possible can pass through the patient in order to achieve an optimally high system imaging quality, under the assumption that the patient to be scanned is completely covered in the scan area.

In a further embodiment of a computed tomography system with an adjustable focal spot-to-detector distance according to the invention a further linear track 70 is provided on the gantry 10 (as shown in the FIGURE). The detector mount 60 is installed on the linear track 70 and can move up and down along the rail of the linear track 70 in order to adjust the distance between the detector mount 60 and the focal spot 42 of the x-ray tube 40. When the x-ray tube 40 and the detector mount 60 are located respectively on the linear track 50 and the linear track 70 and move to the position shown dashed, the distance between the focal spot 42 of the x-ray tube 40 and the detector mount 60 increases to D2, and at this point in time the radius at which x-ray tube 40 and detector rotate expands from R1 to R2. The acquisition field of the CT system consequently increases.

In a further embodiment, the radius of the patient opening 20 can also be adapted. The patient opening 20 is defined at gantry side by an inner enclosure 20' (indicated only by dashes). This inner enclosure 20' can be formed by movement-coupled, overlapping lamella elements that are mounted such that the radius of the patient opening 20 can be increased. When the x-ray tube 40 and the detector mount 60 are located on the linear track 50 and the linear track 70 and move to the position shown dashed, the distance between the focal spot 42 of the x-ray tube 40 and the detector mount 60 increases to D2. The movement-coupled lamella elements are also activated at this point in time, causing the patient opening 20 to expand from a radius R1 to the patient opening 20' with a radius R2, such that a patient to be scanned with a larger volume can be introduced into the gantry 10 for scanning and a better accessibility to the patient to be scanned is achieved.

As described above, the present invention realizes a free adjustment of the distance of the focal spot of the x-ray tube relative to its corresponding detector via installation of an x-ray tube and a detector mount of a CT system on linear tracks on two sides of the gantry, and the following advantages can be achieved:

1. the acquisition field of the CT system can be enlarged with increasing distance between the x-ray tube and the detector mount;
2. via adjustment of the distance between the x-ray tube and the detector mount, more x-rays can effectively penetrate through a subject to be scanned, such that a higher system imaging quality can be attained, and
3. with increased diameter of the patient opening, a subject to be scanned with a larger volume can be inserted into the gantry for scanning or, respectively, greater accessibility to a subject to be scanned can be achieved.

Although modifications and changes may be suggested by those skilled in the art, it is the intention of the inventor to embody within the patent warranted hereon all changes and modifications as reasonably and properly come within the scope of the inventor's contribution to the art.

I claim as my invention:

1. A computed tomography system comprising:
   a gantry having a stationary housing defining a continuous annular patient opening therein;
   an x-ray tube and a detector mounted opposite each other at said gantry with an irradiation region therebetween configured to accommodate an examination subject, said x-ray tube having a focal spot from which x-ray radiation is emitted with a fixed aperture angle; and
   said x-ray tube being mounted at said gantry on a linear track having a rail, and being moveable along said rail of said linear track to selectively change a distance between said focal spot and said detector to change a size of said region.

2. A computed tomography system as claimed in claim 1 comprising a detector mount on which said detector is mounted at said gantry.

3. A computed tomography system as claimed in claim 2 wherein said detector mount comprising a linear track having a rail, with said detector being moveable along said rail of said linear track of said detector mount to participate in changing said distance between said focal spot and said detector to change the size of said region.

4. A computed tomography system as claimed in claim 3 wherein a displacement distance of said detector is determined by controlling a length of said rail of said linear track of said detector mount.

5. A computed tomography system as claimed in claim 1 wherein a displacement distance of said x-ray tube is determined by controlling a length of said rail of said linear track along which said x-ray tube is moveable.

6. A computed tomography system as claimed in claim 1 wherein said gantry comprises an inner enclosure surrounding said patient opening, said inner enclosure being mechanically adjustable to adjust a radius of said patient opening.

7. A computed tomography system as claimed in claim 6 comprising a coupling arrangement that couples adjustment of said inner enclosure with movement of said x-ray tube to set a maximum radius of said patient opening dependent on movement of said x-ray tube.

8. A computed tomography system as claimed in claim 7 comprising a detector mount on which said detector is mounted at said gantry, said detector mount comprising a linear track having a rail along which said detector mount is moveable.

9. A computed tomography system as claimed in claim 8 wherein said coupling arrangement couples adjustment of said inner enclosure to movement of said x-ray tube and to movement of said detector.

10. A computed tomography system as claimed in claim 6 wherein said inner enclosure is comprised of a plurality of movement-coupled, overlapping lamella elements.

* * * * *